United States Patent
Mackie et al.

(10) Patent No.: US 7,302,038 B2
(45) Date of Patent: Nov. 27, 2007

(54) CORRECTION OF PATIENT ROTATION ERRORS IN RADIOTHERAPY USING COUCH TRANSLATION

(75) Inventors: Thomas Rockwell Mackie, Verona, WI (US); Sarah Ann Boswell, Madison, WI (US); Robert Jeraj, Madison, WI (US); Harald Keller, Madison, WI (US); Michael William Kissick, Madison, WI (US); David Pearson, Madison, WI (US); Gustavo Olivera, Madison, WI (US); Kenneth J. Ruchala, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 473 days.

(21) Appl. No.: 10/949,831

(22) Filed: Sep. 24, 2004

(65) Prior Publication Data

US 2006/0072699 A1    Apr. 6, 2006

(51) Int. Cl.
*G21K 5/10*     (2006.01)
*A61N 5/10*     (2006.01)

(52) U.S. Cl. .......................................... 378/69; 378/65

(58) Field of Classification Search .................. 378/68, 378/69, 65
See application file for complete search history.

(56) References Cited

U.S. PATENT DOCUMENTS

| | | | |
|---|---|---|---|
| 5,207,223 A * | 5/1993 | Adler ........................... | 600/427 |
| 5,427,097 A * | 6/1995 | Depp ........................... | 600/427 |
| 5,446,548 A * | 8/1995 | Gerig et al. ................. | 356/620 |
| 5,673,300 A * | 9/1997 | Reckwerdt et al. ........... | 378/65 |
| 5,754,623 A * | 5/1998 | Seki ............................. | 378/65 |
| 5,815,547 A * | 9/1998 | Shepherd et al. ............. | 378/65 |
| 6,307,914 B1 * | 10/2001 | Kunieda et al. .............. | 378/65 |
| 6,385,288 B1 * | 5/2002 | Kanematsu ................... | 378/65 |
| 6,416,219 B1 * | 7/2002 | Pflaum et al. ............... | 378/209 |
| 6,516,046 B1 * | 2/2003 | Frohlich et al. .............. | 378/65 |
| 6,914,959 B2 * | 7/2005 | Bailey et al. ................. | 378/65 |
| 7,016,522 B2 * | 3/2006 | Bani-Hashemi ............. | 382/131 |
| 2004/0096033 A1 * | 5/2004 | Seppi et al. .................. | 378/65 |
| 2004/0218719 A1 * | 11/2004 | Brown et al. ................. | 378/95 |

OTHER PUBLICATIONS

P.M. Evans, et al., Technical Note: The implementation of patient position correction using a megavoltage imaging device on a linear accelerator, 1993, The British Journal of Radiology, 66, 833-838. Sutton, Surrey U.K.

Mohammad Amin Mosleh-Shirazi, et al., A cone-beam megavoltage CT scanner for treatment verification in conformal radiotherapy, Radiotherapy and Oncology 48 (1998) 319-328, Elsevier Science Ireland Ltd.,

* cited by examiner

*Primary Examiner*—Edward J. Glick
*Assistant Examiner*—Thomas R. Artman
(74) *Attorney, Agent, or Firm*—Boyle Fredrickson Newholm Stein & Gratz S.C.

(57) ABSTRACT

Compensation for patient rotation between planning and treatment in a radiation therapy machine is provided by angled translation of a table surface on which the patient is supported without actual patient rotation.

21 Claims, 4 Drawing Sheets

CORRECTION OF PATIENT ROTATION ERRORS IN RADIOTHERAPY USING COUCH TRANSLATION

CROSS-REFERENCE TO RELATED APPLICATIONS

STATEMENT REGARDING FEDERALLY SPONSORED RESEARCH OR DEVELOPMENT

This invention was made with United States government support awarded by the following agencies: NIH CA88960. The United States has certain rights in this invention.

BACKGROUND OF THE INVENTION

This invention relates generally to radiation therapy equipment for the treatment of tumors or the like and, in particular, to a method of aligning a patient with a previously prepared radiation treatment plan.

In external source radiation therapy, a radiation source external to the patient projects a beam of radiation toward a treatment region. The radiation beam may be x-rays or electrons from a linear accelerator in the range of two to twenty-five MeV or gamma rays from highly focused radioisotopes such as $^{60}$Co.

Typically, the tumor will be treated from a number of different angles with the intensity and/or shape of the radiation beam adjusted for each angle. Multiple beams converging on the site of a tumor reduce the dose of radiation received by surrounding non-tumorous tissue and skin and the adjustment of the intensity of radiation at each angle allows irregular tumors to be treated while minimizing the irradiation of sensitive structures near the tumor site. The angles and intensities of the radiation beams for treating a tumor together form a "treatment plan".

One highly accurate technique of radiation therapy uses a radiation source that produces a fan beam in which the spatial distribution of the intensities may be controlled. The radiation source orbits so that the fan beam illuminates a slice of the patient while the intensity of each small region of the fan beam is modulated as a function of that angle. By properly selecting the beam intensities at different angles, complex regions within the slice or slices may be accurately irradiated. U.S. Pat. No. 5,317,616 issued May 31, 1994, and assigned to the same assignee as the present application, describes the construction of such machines and methods of calculating the necessary beam intensities as a function of angle. Here the treatment plan is a "sinogram" of intensities as a function of angle.

In order to take advantage of the improved accuracy offered by such radiation therapy systems, the treatment plan may be developed using x-ray images of the patient and tumor, either a set of computed tomography ("CT") images or conventional x-ray images taken at different angles about the patient.

A physician may outline the tumorous area on the x-ray images and then use a computer program that selects the beam angles based on desired dose limits for the tumor region.

The patient may not have the same position on a machine used to acquire images used in treatment planning as they have on the radiation therapy machine. Shifts in patient position are inevitable in treatments that require multiple sessions separated in time and even when the same machine can be used to image the patient and provide radiation therapy, the patient may move slightly in the time it takes to complete the treatment planning.

To address the problem of patient movement, U.S. Pat. No. 5,673,300, also assigned to the assignee of the present invention, describes a method of determining movement of the patient by obtaining one or more x-ray images at the time of treatment and comparing them to the planning images. The treatment plan may then be modified according to the known displacement of the patient or the patient repositioned.

Particularly for sophisticated treatment plans describing many individually modulated radiation beams, changes of the treatment plan to accommodate patient movement can be difficult. On the other hand, repositioning of the patient on the treatment table is also a problem both because it is difficult to gauge how far the patient must be moved (without multiple verification images) and because it may encourage additional movement and/or be difficult or uncomfortable for the patient.

Some movements of the patient, for example, along the axis of movement of the table or in elevation may be corrected mechanically by changing the elevation of the table or its axial position. Changes in angle of the patient with respect to the table axis, for example, in roll may be corrected simply by offsetting the angle of the treatment plan.

On the other hand, angular motion of the patient about a vertical axis (yaw) or a horizontal axis (pitch) cannot be so easily compensated with standard tables. Adding pitch or yaw motions to a table would be prohibitively expensive and by angling the table out of axis increases the possibility of interference between the table and the radiation therapy machine. Any motion that tips the patient from horizontal can cause undesirable motion of internal organs and possibly patient discomfort.

SUMMARY OF THE INVENTION

The present invention corrects for pitch and/or yaw movement of a patient, without a compensating pitch and/or yaw rotation of the table, through a "crab-wise" or diagonal table motion. This crab-wise motion avoids the need for complex table mechanisms, repositioning of the patient on the table, or undesirable changes in gravitational orientation.

In one embodiment, the present invention provides a radiation therapy machine having a radiation source directing a radiation therapy beam at least at a plurality of angles within a treatment plane. A mechanized patient table is movable through the treatment plane, providing horizontal motion along an axis diagonal to a normal to the treatment plane.

It is one object of at least one embodiment of the invention to provide a table that may move diagonally with respect to a treatment plane to compensate for rotation of a patient.

It is another object of at least one embodiment of the invention to provide a correction for rotation of the patient without actual rotation of the table such as might create interference between the radiation therapy machine and the table or patient discomfort.

The table may provide a first mechanism providing translative movement along the normal and a second mechanism providing translative movement horizontal and perpendicular to the normal.

Thus, it is an object of one embodiment of the invention to provide for diagonal table movement without the need for a complex drive mechanism.

A table controller may provide signals to the first and second mechanisms that control the relative rate of translation effecting different angles of horizontal, diagonal motion.

Thus, it is another object of at least one embodiment of the invention to provide a simple mechanism that can produce a variety of different diagonal motions.

The table controller may provide signals to the first and second mechanisms that change the angle of the diagonal motion as a function of a position of the table along the axis.

Thus it is an object of at least one embodiment of the invention to provide a correction not only for uniform patient offsets but for bends or twists that can be approximated by successive piecewise diagonal motion.

The table may further provide motion components in a vertical plane whereby the table surface may be moved with a vertical diagonal motion.

It is thus another object of at least one embodiment of the invention to provide a method of correcting for pitch rotation errors that does not require reorientation of the patient with respect to gravity.

The radiation therapy machine may include an x-ray source and detector positioned across the normal for making an x-ray image of the patient positioned along the axis.

Thus, it is another object of at least one embodiment of the invention to provide a system that works with tables that may be further constrained in movement by mechanisms for imaging.

The system may include a computer executing a stored program to receive a planning x-ray image and a treatment x-ray image to deduce rotation of the patient between acquisition of the planning x-ray image and the treatment x-ray image and to control the diagonal motion of the patient table to compensate for that rotation.

Thus, it is another object of at least one embodiment of the invention to provide an extremely rapid correction for patient offsets that may be processed while the patient remains on the same table where the treatment x-ray image is acquired.

The treatment image and the planning image may be CT-type images or conventional radiographic-type images.

Thus, it is another object of at least one embodiment of the invention to provide a system that may flexibly accept a variety of different measures of patient offset measurements.

The computer may scale the stored radiation treatment plan in the direction perpendicular or in the plane of the radiation treatment plan by a function of the deduced rotation.

Thus, it is another object of at least one embodiment of the invention to provide for scaling correction of errors introduced by the piece-wise approximation of pitch or yaw offset.

The controller of movement of the table may be substantially continuous during the radiation therapy or may be interleaved with the radiation therapy treatment.

Thus, it is another object of at least one embodiment of the invention to provide a system that works both with conventional and helical radiation therapy systems.

The controller may control the relative rates of couch translation and rotation of the radiation source through the plurality of angles by changing either the couch translation rate or the source rotation rate by a constant factor or as a function of table position.

Thus it is another object of at least one embodiment of the invention to provide a simple correction for changing patient "twist" (rotation in the imaging plane) over the length of the table.

The controller may control a translation rate of the table axis while maintaining a predetermined relationship between gantry angle, table location, and collimator (MLC) configurations, thus varying the amount of radiation (number of linear accelerator pulses) delivered at each location within the patient.

Thus it is another object of at least one embodiment of the invention to provide a simple method of compensating for radiation source variations or to provide a common mode modulation of the rays of radiation.

These particular objects and advantages may apply to only some embodiments falling within the claims and thus do not define the scope of the invention.

DETAILED DESCRIPTION OF THE PREFERRED EMBODIMENT

Figure 1:
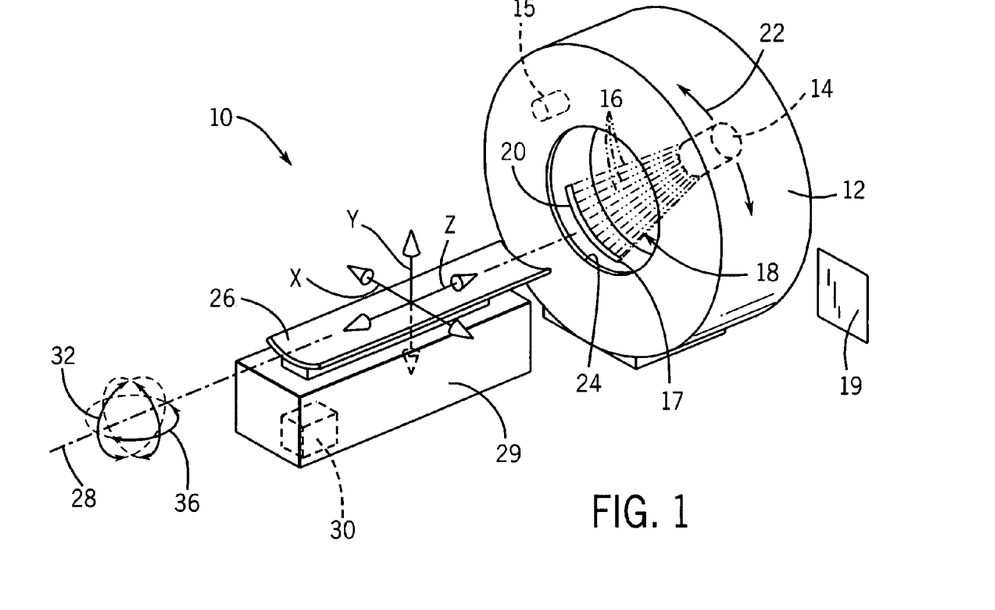
FIG. 1 is a simplified perspective view of a radiation therapy system employing a table that may move in three orthogonal directions and can be used in the present invention to correct for rotation offsets.
Figure 2:
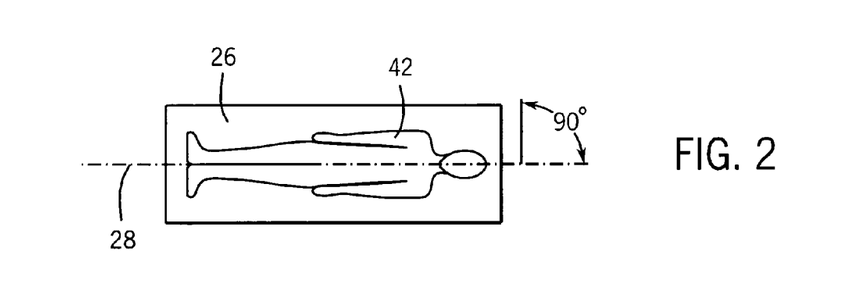
FIG. 2 is a simplified top plan view of a patient on the table of the radiation therapy machine of FIG. 1 showing alignment of the patient during a treatment-planning scan.

Referring now to FIGS. 1 and 2, a radiation therapy machine 10 suitable for use with the present invention may include a gantry unit 12 holding a radiation source 14 to project a set of intensity modulated rays 16, forming a therapeutic radiation beam 18, toward a target 20 such as may be a portal imaging device, an array of CT detectors, or a radiation stop.

During use, the radiation source 14 follows an orbit 22 about a bore 24 through which a patient 42 may pass supported on the surface of a table 26. The table 26 may pass through the bore 24 generally perpendicularly to a treatment plane 19 containing orbit 22.

The gantry unit 12 may also include an opposed x-ray source 15 and detector 17 for acquiring CT or scout scan-type images according to techniques well known in the art.

The table 26 may be supported by a pedestal unit 29 including a mechanism (to be described below) allowing for table motion: (1) along the table axis 28 in the z-direction, (2) along a vertical axis in the y direction, and (3) horizontally and perpendicularly to the table axis 28 in the x-direction. The pedestal unit 29 may include control electronics 30 or be controlled by a central controller used for the entire radiation therapy machine 10.

As will be described in more detail below, the table 26 may be moved during treatment of the patient 42 so as to correct for a variety of rotation offsets of the patient including pitch 32 in which the head or feet of the patient 42 are respectively raised or lowered and yaw 36 in which the patient is rotated about the y-axis.

Figure 9:
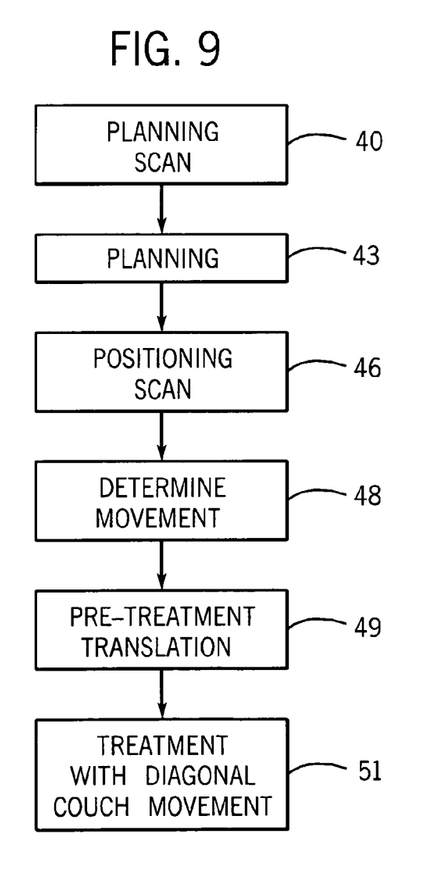
FIG. 9 is a flowchart showing the steps of the method of the present invention.

Referring now to FIGS. 2 and 9, at a first step in a radiation therapy process indicated by process block 40, the patient 42 may be positioned on the table 26 (or on the table of a separate imaging machine not shown) with the patient's head and feet aligned generally with the table axis 28. At this time a planning scan is obtained as will be described below and such as consists of one or more x-ray tomography images of the patient 42, where the image plane lies along the x-y-axis, or one or more projection images where the image plane is parallel to the table axis 28. The images acquired at process block 40 will be termed the planning images.

As indicated by process block 43, the planning images are then used to prepare a treatment plan by identifying within the images the shape and location of the tumor. This information is used to develop a set of intensities for the rays 16 of the radiation beam 18 at different angles to effectively treat the tumor.

Figure 3:
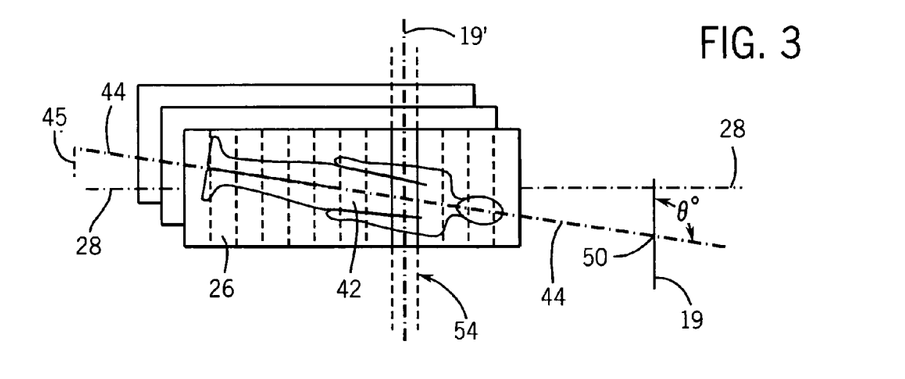
FIG. 3 is a view similar to that of FIG. 2 showing positioning of the patient with highly exaggerated yaw offset during treatment and showing motion of the table through the radiation treatment plane to correct for that yaw offset.

Referring now to FIG. 3, at a later time the patient 42 is positioned on the table 26 in preparation for the radiation treatment and second positioning images are taken either using CT or radiographic images. This acquisition is indicated by process block 46 of FIG. 9.

Per process block 48, the positioning images may then be used to determine rotation of the patient 42 with respect to a planning position of the patient 42 corresponding to an assumed location of the patient 42 with respect to the gantry unit 12 during acquisition of the planning images. A translative offset may also be determined at this time so as to center the first treatment slice within the gantry.

One method of determining rotation of the patient between the times of the planning and treatment images is described in U.S. Pat. No. 5,673,300 which makes use of CT images describing volume planning and treatment images. Rotation is deduced from these images by distorting one image through rotation, translation, and the like, one until it fits with the other. More generally, pairs of CT slice images may be fit to each other to determine relative offsets for that particular slice and the corrections of the present invention may be made on a slice-by-slice basis rather than attempting to extract a global offset of the tumor.

Referring to FIG. 3, the patient 42 may have, for example, a yaw rotation of $\theta$ with respect to the assumed planning position as determined above. This yaw must be corrected for the treatment plan based on the planning position to be valid. In a first embodiment of the invention in which the table 26 cannot rotate about any of the axes x, y or z, this yaw $\theta$ is corrected by an equal angular offset $\theta$ of a path of translation 50 of the table 26 through the treatment plane 19.

Generally, for a yaw of $\theta$ in patient position, as shown in FIG. 3, the table 26 must be translated along centering axis 45 prior to radiation delivery so that the superior end of the tumor is centered in the beam. This centering is indicated by process block 49. Generally, the initial translation will be proportional to the sine of the angle of offset with respect to patient axis 44' times the distance between the center of rotation used in determining the translational and rotational setup offsets and the then current slice.

After this centering translation and during radiation delivery the table must move along a path of translation of angle $\theta$ equal to the yaw angle $\theta$ with respect to the treatment plane 19.

As the patient 42 moves along the path of translation 50 the patient 42 will move both along the y-axis and x-axis, the latter motion generally centering of the patient 42 within the bore 24 at the treatment plane 19. The width of the beam 18 along the treatment plane 19 defines a series of treatment slice 54 each with a different x-axis offset and the table may move between the treatment of each slice in a step and treat fashion.

Figure 4:
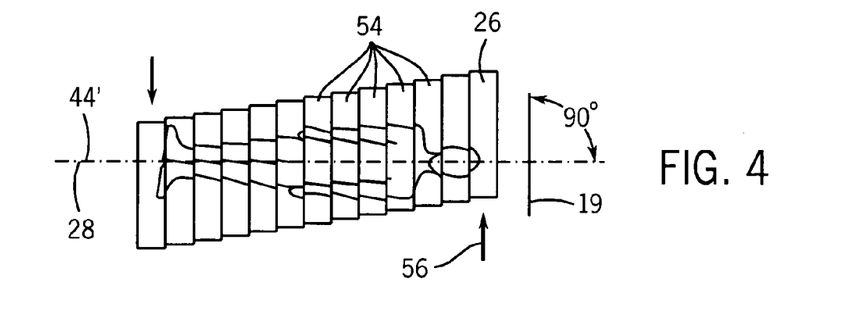
FIG. 4 is a composite of treatment slices of the patient viewed from a fixed location in the radiation treatment plane showing the piece-wise correction of yaw of the patient.

Referring now to FIG. 4, the effect of the x-axis motion from the point of view of the radiation therapy machine 10 is that the patient has been divided into a number of slices 54 that have been moved in the x-axis direction as indicated by arrow 56 (in fact the cause by underlying couch motion along path of translation 50) so as to realign the patient along the table axis 28. This x-axis motion causes piecewise realignment of the patient 42 along a new patient axis 44' identical to table axis 28 through an effective shifting of slices of the patient 42 with respect to their neighbor slices along the x-axis through x-axis movement of the table.

This altered movement of the table 26 along a diagonal path of translation 50 is indicated in FIG. 9 as process block 51. The path of translation 50 may be essentially continuous or may be obtained in a stepwise fashion with axial motion along table axis 28 alternating with lateral motion across table axis 28.

It will be understood from this example and the discussion associated with FIGS. 2 through 4 that a similar correction may be provided for rotation of the patient in pitch where the patient's head or feet have been shifted in relative elevation. In this case, the path of translation 50 is in a vertical plane with the elevation of the table 26 changing as the table moves along the table axis 28.

Correction of roll of the patient rotation about axis z can be performed simply by changing the relative phase of the treatment sinogram, something which can be accomplished in real time without patient repositioning.

Additional offsets of the patient may be corrected through simple translations along the x, y, and z-axis.

In an alternative embodiment, the treatment of the patient 42 may be performed on a continuous helical basis with continuous motion of the table 26 along the path of translation 50 rather than motion of the table 26 being confined to periods in between orbits of the radiation source 14.

As is evident from the exaggerated depiction of FIG. 4, the correction of the positioning of the patient 42 to lie along patient axis 44' without rotation of the table 26 results in a slight discontinuity between the treatment slices 54. Generally, for small angles likely to be seen in practice and for tumor locations not far from axis 28, these discontinuities can be disregarded.

Figure 5:
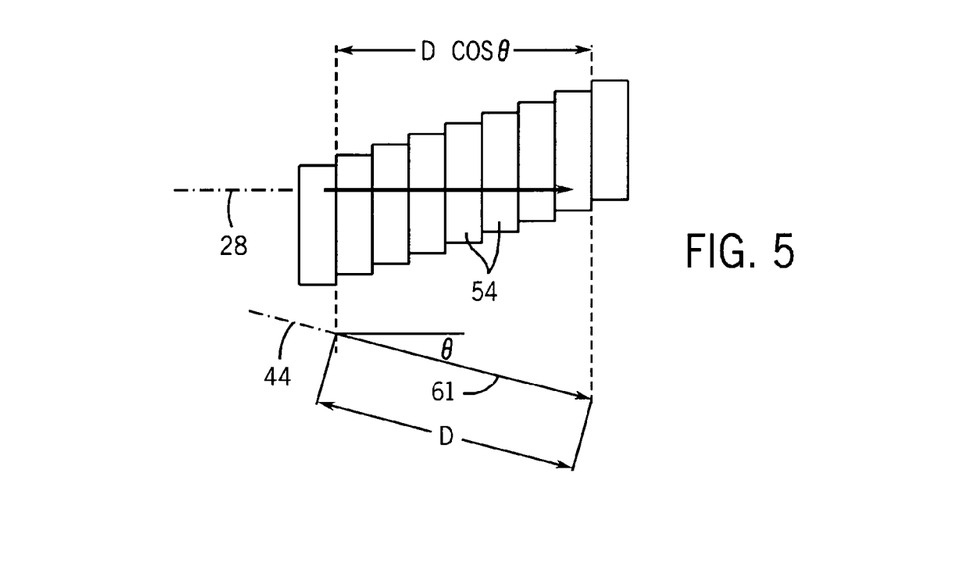
FIG. 5 is a simplified view of FIG. 4 showing a geometric foreshortening of the patient by the process of FIG. 4 such as may be corrected with a scaling factor.

Referring now to FIG. 5, the realignment shown in FIG. 4 also provides a slight compression to the patient caused by a geometric projection of the patient length 61 onto the table axis 28 from the slicing process. Thus, if the patient length 61 along the patient axis 44 is of length D and shifted with respect to table axis 28 by angle θ, then the reconstructed patient from the slices 54 will have an apparent length of D cosine (θ). Similarly, if the patient width is W, the reconstructed patient from slices 54 will have an apparent width of W/cosine (θ). Most importantly, we also neglect an x-dependent shear along the z-axis.

This compression in D and stretching in W have been found to be negligible even in the case of very long treatment areas. The error due to neglecting shear in the z-direction may prove to be significant for wide treatment areas where the error accumulates. Correction of the treatment plan to accommodate scaling is relatively simple and can be done in real time with the patient on the table and can be done by a resampling of sinogram data with interpolation. Correction of the treatment plan can also be done to reduce any residual shear as is described generally in U.S. Pat. No. 5,673,300 entitled: "Method of Registering a Radiation Treatment Plan to a Patient", hereby incorporated by reference.

Figure 6:
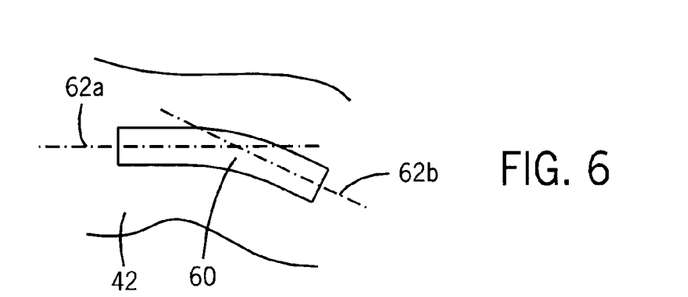
FIG. 6 is a detailed view of a treatment zone within a patient subject to a bending distortion in which the treatment zone follows two axes of different pitch or yaw such as may be accommodated by the present invention.

Referring now to FIG. 6, a tumor 60 within the patient 42 may have a bend characterized by an alignment of portions of the tumor with different axes 62a and 62b, either or both of which may represent angular rotations about any of the axes x and y with respect to the planning image. The present invention may accommodate such bend configurations (something which cannot be done by a static rotation of the table were that possible) simply by changing the angle of the diagonal path of translation 50 of the table during the radiation treatment process.

Figure 7:
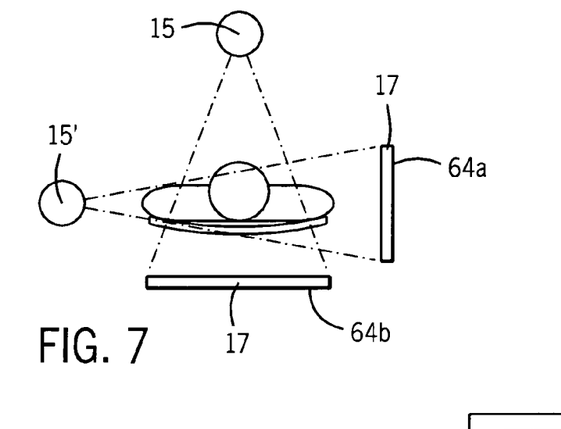
FIG. 7 is a view of the patient in front elevation showing the acquisition of two projection x-rays for deducing patient offset.
Figure 8:
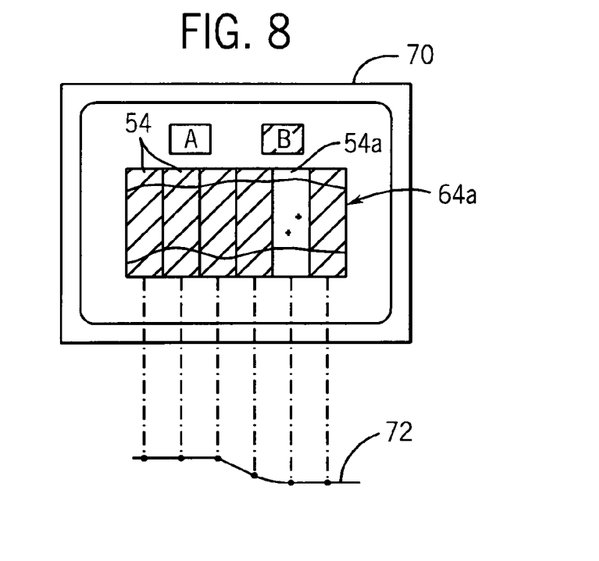
FIG. 8 is a display of the scans of FIG. 7 such as may be used to deduce offset of the tumor caused by patient movement.

Referring now to FIGS. 7, 8 and 9, in a simplified method of deducing patient movement per process block 48, two radiographic type images: an anterior/posterior (AP) image 64a and a lateral image 64b may be acquired using conventional x-ray equipment or the CT equipment described above in a scanning mode. A planning and treatment image is obtained in each orientation.

The planning and treatment images, for example lateral images 64a, may then be alternately displayed on a display device 70 associated with the control of the radiation therapy machine 10. Specifically, the image may be divided into slices 54 representing, for example, the width of the treatment beam and the user may rapidly switch between the planning or treatment version of each slice. The switching allows an operator to align the two sliced images and thus to deduce an offset perpendicular to the orientation of the image. More usually, the images are viewed together as alternating pixels or groups of pixels from each respective image. For images in the lateral direction, AP offsets can be determined on a slice-by-slice basis and for images in the AP direction lateral offsets can be determined on a slice-by-slice basis.

The series of offsets 72 for each separately aligned slice provides a rotation value (based on the slope of the series of offsets 72) which may be used to provide an angle value used to control movement of the table 26. Alternatively, the series of offsets 72 may directly control lateral or elevational movement of the table 26 without the intervening step of deducing an angle. Here lateral offset controls x-axis movement of the table and AP offset controls y movement of the table as described above. Such direct control allows simple correction of non-rigid body patient movement as described with respect to FIG. 6.

Clearly, the process of comparing slices 54a in the lateral and AP images can be automated by using image shifting and correlation algorithms well known in the art and image orientations other than lateral and AP may be used, although preferably orthogonal image orientation, that match the movement axes of the table 26 are used.

Figures 10, 11, 12:
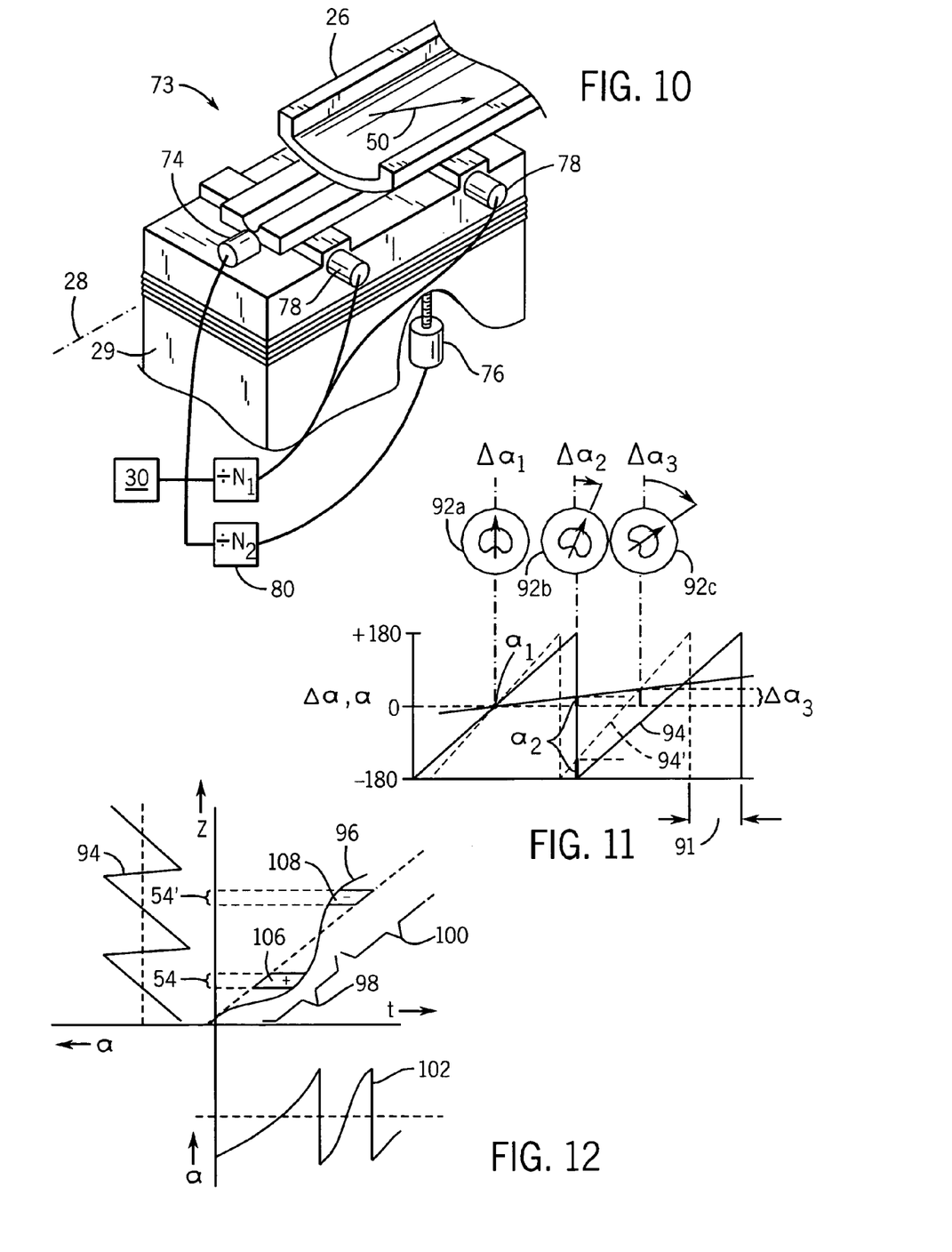
FIG. 10 is a fragmentary view of a mechanism for implementing the necessary table motions with linear stages.
FIG. 11 is a plot of gantry rotation angle $\alpha$ as a function of z-axis table location superimposed on a plot of patient twist $_{\Delta\alpha}$ as a function of z-axis table location showing correction for twist.
FIG. 12 are interfitting plots of gantry rotation angle $\alpha$ as a function of z-axis table location, z-axis table location as a function of time, and gantry rotation angle $\alpha$ as a function of time showing how changing z-axis velocity may change the effective radiation exposure to the patient.

Referring now to FIG. 10, the present invention contemplates the use of a table motion system 73 in which table 26 is moveable along the table axis 28 by an axial linear stage 74 of a type well known in the art. Table elevation may be controlled by one or more motorized screws 76 of a type also well known in the art or other mechanisms commonly found on tables of this kind.

The present invention adds lateral linear stages 78 positioned between the axial linear stage and the pedestal unit 29 allowing for x-axis motion of the table 26. The lateral linear stages 78 together with the axial linear stage 74 and the motorized screws 76 to provide the ability to move the table 26 along an arbitrary path of translation 50 at an angle to axis 28 having components in a vertical and/or horizontal direction in either a continuous or step-wise fashion.

Generally, for a path of translation 50 of constant angle to the axis 28, the angle of the path of translation 50 may be controlled simply by changing a proportion between the motors associated with the axial linear stage 74, lateral linear stages 78, and motorized screws 76. For stepping motors, this control may be accomplished with a pair of dividers 80 of different divisors as is well understood in the art. Very simple control electronics may produce a wide variety of different angles and offsets.

Referring now to FIG. 11, the present invention may be used to correct not only for offsets of the patient 42 in x, y, and z as described above, but twist of the patient 42, being varying rotation about the z-axis as a function of location along the z-axis. This twist, termed herein $_{\Delta\alpha}$, is the angular difference about the z-axis for each slice 54 of the patient 42 between the position of the patient 42 during treatment and the position of the patient 42 at the time of the planning image.

Using a similar technique to that described above with respect to FIG. 8, twist $_{\Delta\alpha}$, may be deduced by comparing tomographic slices of the patient 42 taken for treatment planning and similar slices taken with the patient positioned for radiation treatment. The lateral and AP views of FIG. 8 are thus changed to tomographic views so as to deduce angular rotation. A correlation or visual comparison of these images with different degrees of rotation about the z-axis will reveal Δα for each slice between treatment planning and actual treatment.

This amount of twist $_{\Delta\alpha}$, which may vary as a function of z-axis location, may be plotted as a series of twists 90 similar to the series of offsets 72 previously described above. Thus, for example, a first slice 92a may have essentially no twist providing a $_{\Delta\alpha_1}$ of zero, while a second slice 92b further along the z-axis may provide a first amount of counterclockwise twist $_{\Delta\alpha_2}$ and a third slice 92c may provide a second amount of counterclockwise twist $_{\Delta\alpha_3}$.

Generally, during radiation treatment, the gantry unit 12 will provide a cyclic gantry spatial trajectory 94 describing gantry angle $_\alpha$ of the radiation source 15 as a function of z-axis location. For a conventional, helical scan with motion of the table 26, this gantry spatial trajectory 94 will be a sawtooth function. As will be apparent from this figure, the series of twists 90 may be accommodated by an advancing (or retarding) of the phase 91 of the gantry spatial trajectory 94 at each slice by an angular amount exactly corresponding to the value of the series of twists 90 at that slice.

Generally, the series of twists 90 will be continuous (because the patient is physically continuous), and thus a continuously variable phase correction (interpolating between measurements of twist at each slice) may be applied to the gantry spatial trajectory 94 by slight incremental changes in gantry rotational speed with respect to the table 26 z-axis translation speed. This phase correction need not be a linear function of z, but may accommodate complex twist functions using well known curve fitting interpolation techniques.

This correction for twist may be used independently of the techniques for offset correction described above or in conjunction with them, and does not require any special table mechanism. Referring momentarily to FIG. 10, the control electronics 30 may coordinate this variation of the relationship between rotational rate of the gantry and translation rate of the table 26, for example, by implementing a divider similar to dividers 80. Preferably the gantry unit 12 maintains the same rotational speed and the table motion is slowed or speeded.

In yet another embodiment of the invention, changing the absolute speed of the table 26 along the z-axis (or in the more general case along any diagonal) while maintaining a predetermined relationship between gantry angle and table z-axis location and collimator (MLC) configurations can be used to change or adjust the exposure of the patient 42 for a given slice 54 or portion of the slice 54 without altering the other aspects of treatment. This technique can be used to impose a secondary modulation onto the radiation (across all rays 16), for example, to make corrections for the scaling errors noted above, or to correct for variations in output of the radiation source 15 or the like.

Referring to FIG. 12 in a simple embodiment, the cyclic gantry spatial trajectory 94 (plotted vertically as a function of z-axis location) remains regular, that is, with constant spatial phase and frequency. The table z-axis position 96 (plotted horizontally as a function of time) is varied, however, to have retarded intervals 98 and advanced intervals 100.

This change in table velocity causes a distortion of gantry time trajectory 102, however, this distortion does not affect the fundamental geometry of the treatment plan. On the other hand for a given slice 54, the retarded intervals 98 will cause an increase 106 in the exposure time of the slice 54 whereas the advanced intervals 100 will cause a decrease 108 in the exposure time for a slice 54'.

For a constant output from source 15, this change in exposure time effects an increase or decrease in dose, respectively, of the patient 42 at that slice. For a varying output from source 15, this change in exposure time may be used to correct for fluctuations in the output from source 15. This exposure time control technique may be used alone or in conjunction with the twist correction and/or the offset correction described above.

It will be understood from the above description that the present invention may be used in conjunction with modifications of the treatment plan, for example to correct for roll, according to the particular time constraints and processing resources available for such treatment plan modifications. Further the invention may be used in conjunction with the table that provides some rotation, for example, in yaw, where the invention augments this correction and/or works in pitch.

It is specifically intended that the present invention not be limited to the embodiments and illustrations contained herein, but include modified forms of those embodiments including portions of the embodiments and combinations of elements of different embodiments as come within the scope of the following claims.

We claim:

1. A radiation therapy machine comprising:
   a radiation source directing a radiation therapy beam at a plurality of angles within a treatment plane;
   a mechanized patient table movable through the treatment plane, the table providing motion having components both along a normal to the treatment plane and at lease one direction perpendicular to the normal; and
   a table controller controlling an absolute translation rate of the table independently of relative rates of table motion and rotation of the radiation source through the plurality of angles to vary a treatment time of different slices of a patient.

2. The radiation therapy machine of claim 1 wherein the table controller further varies a relative rotational rate of the radiation source through the plurality of angles with respect to table movement.

3. The radiation therapy machine of claim 1, wherein the table controller controls the relative rates of table motion and rotation of the radiation source through the plurality of angles, wherein the machine is configured to compensate for patient twist.

4. The radiation therapy machine of claim 3, wherein the table motion is one of increased and decreased while the rotation of the radiation source remains constant.

5. A radiation therapy machine comprising:
   a radiation source directing a radiation therapy beam at a plurality of angles within at least one treatment plane;
   a mechanized patient table movable through the treatment plane, the table providing substantially continuous motion in a vertical plane diagonal to a normal to the treatment plane; and
   a controller communicating with the patient table and the radiation source to move the table at an angle with respect to the normal in a vertical plane during treatment of a patient with the radiation therapy beam.

6. The radiation therapy machine of claim 5 wherein the table provides a first mechanism providing translative movement along the normal and a second mechanism providing translative movement vertically perpendicular to the normal.

7. The radiation therapy machine of claim 6 wherein the controller provides signals to the first and second mechanism to control relative rates of translation effecting different angles of vertical diagonal motion.

8. The radiation therapy machine of claim 5 wherein the controller controlling the table to provide vertical diagonal motion at an angle relative to the normal that changes as a function of position of the table along the normal.

9. The radiation therapy machine of claim 5 further including an x-ray source and detector positional across the normal for making an x-ray image of a patient positioned along the normal.

10. The radiation therapy machine of claim 9 wherein the controller executes a stored program to receiving a planning x-ray image and a treatment x-ray image to deduce rotation of the patient between acquisition of the planning x-ray image and the treatment x-ray image and to control the diagonal motion of the patient table to compensate for the rotation.

11. A radiation therapy machine comprising:
    a table surface for supporting a patient;
    a radiation source directing a radiation therapy beam at the patient on the table surface from a plurality of angles along a treatment plane;

a radiation detector receiving an imaging data along an imaging plane substantially parallel to the treatment plane to acquire a current image of the patient intersected by the imaging plane;

a computer executing a stored program to receive the current image of the patient to deduce a rotation of the patient with respect to a stored previous position of the patient used for treatment planning;

a controller adjusting movement of the radiation therapy machine to compensate for the deduced rotation; and a table movement mechanism wherein the controller moves the table surface through the treatment plane at an angle compensating for the deduced rotation;

wherein the stored program provides a matching between the current image of the patient and a stored planning image of the patient at a previous positioning of the patient, the matching providing an offset amount indicating a shifting of a patient along the treatment plane;

wherein the deduced rotation of the patient is a series of offsets as a function of movement of the patient through the treatment plane; and wherein the control of the patient table provides movements of the patient table along the treatment plane as a function of axial movement of the table through the treatment plane to counteract the series of offsets.

12. The radiation therapy machine of claim 11 wherein the current image and the stored planning image have an image plane perpendicular to the radiation treatment plane.

13. The radiation therapy machine of claim 11 wherein the current image and the stored planning image are tomographic images having an image plane parallel to the radiation treatment plane.

14. The radiation therapy machine of claim 11 wherein the table movement mechanism moves the table by concurrent movement of the table through and perpendicular to the radiation treatment plane.

15. The radiation therapy machine of claim 11 wherein the table movement mechanism moves the table by rotation of a table axis about a vertical axis and movement of the table along the table axis.

16. The radiation therapy machine of claim 11 wherein movement of the table is substantially continuous during substantially continuous movement of the radiation therapy beam through a plurality of angles.

17. A radiation therapy machine comprising:

a table surface for supporting a patient;

a radiation source directing a radiation therapy beam at the patient on the table surface from a plurality of angles along a treatment plane;

a radiation detector receiving an imaging data along an imaging plane substantially parallel to the treatment plane to acquire a current image of the patient intersected by the imaging plane;

a computer executing a stored program to receive the current image of the patient to deduce a rotation of the patient with respect to a stored previous position of the patient used for treatment planning;

a controller adjusting movement of the radiation therapy machine to compensate for the deduced rotation;

a table movement mechanism wherein the controller moves the table surface through the treatment plane at an angle compensating for the deduced rotation; and wherein the computer scales a stored radiation treatment plan in a direction perpendicular or parallel to the radiation treatment plane by a function of the deduced rotation.

18. A method of performing radiation therapy comprising the steps of:

directing a radiation therapy beam at a plurality of angles within a radiation treatment plane;

contemporaneously moving a patient through the radiation treatment plane along a diagonal to a normal to the radiation treatment plane; and controlling an absolute translation rate of the patient independently of relative rates of table motion and rotation of the radiation source through the plurality of angles to vary a treatment time of different slices of a patient.

19. The method of claim 18 further including the step of:

varying a relative rotational rate of the radiation source through the plurality of angles with respect to table movement.

20. The method of claim 18 further including the step of:

changing a treatment plan controlling the radiation beam to accommodate at least one of shear and scaling of the patient caused by the diagonal motion.

21. A radiation therapy machine comprising:

a radiation source directing a radiation therapy beam at a plurality of angles within a treatment plane;

a mechanized patient table movable through the treatment plane, the table providing motion having components both along a normal to the treatment plane and at lease one direction perpendicular to the normal; and a controller controlling an absolute rotation rate of the radiation source independent of relative rates of table motion through the plurality of angles to vary a treatment time of different slices of a patient.

* * * * *

UNITED STATES PATENT AND TRADEMARK OFFICE
CERTIFICATE OF CORRECTION

PATENT NO. : 7,302,038 B2  Page 1 of 1
APPLICATION NO. : 10/949831
DATED : November 27, 2007
INVENTOR(S) : Mackie et al.

It is certified that error appears in the above-identified patent and that said Letters Patent is hereby corrected as shown below:

IN THE CLAIMS

CLAIM 1         Replace "lease" with --least--.
Col. 10, line 10

CLAIM 21        Replace "lease" with --least--.
Col. 12, line 43

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,302,038 B2
APPLICATION NO. : 10/949831
DATED : November 27, 2007
INVENTOR(S) : Thomas Rockwell Mackie et al.

Page 1 of 1

It is certified that error appears in the above-identified patent and that said Letters Patent is hereby corrected as shown below:

In the Specification

Column 1, Lines 11-13:
Delete the phrase:
"This invention was made with United States government support awarded by the following agencies: NIH CA88960. The United States has certain rights in this invention."

And replace with:
--This invention was made with government support under CA088960 awarded by the National Institutes of Health. The government has certain rights in the invention.--.

Signed and Sealed this
First Day of December, 2020

Andrei Iancu
*Director of the United States Patent and Trademark Office*